(12) United States Patent
Lippert (10) Patent No.: US 12,318,523 B2
(45) Date of Patent: Jun. 3, 2025

(54) METHOD FOR IDENTIFYING THE TYPE OF A MEDICAL FILTER, AND APPARATUSES

(71) Applicant: Fresenius Medical Care Deutschland GmbH, Bad Homburg (DE)

(72) Inventor: Nicolas Clemens Lippert, Erding (DE)

(73) Assignee: Fresenius Medical Care Deutschland GmbH, Bad Homburg (DE)

(*) Notice: Subject to any disclaimer, the term of this patent is extended or adjusted under 35 U.S.C. 154(b) by 276 days.

(21) Appl. No.: 18/025,520

(22) PCT Filed: Sep. 15, 2021

(86) PCT No.: PCT/EP2021/075284
§ 371 (c)(1),
(2) Date: Mar. 9, 2023

(87) PCT Pub. No.: WO2022/058329
PCT Pub. Date: Mar. 24, 2022

(65) Prior Publication Data
US 2023/0330314 A1 Oct. 19, 2023

(30) Foreign Application Priority Data
Sep. 18, 2020 (DE) .......................... 102020124395.2

(51) Int. Cl.
*A61M 1/34* (2006.01)
*A61M 1/16* (2006.01)

(52) U.S. Cl.
CPC ........ *A61M 1/3403* (2014.02); *A61M 1/1601* (2014.02); *A61M 2205/18* (2013.01);
(Continued)

(58) Field of Classification Search
CPC ........ A61M 1/16; A61M 1/1601; A61M 1/34; A61M 1/3403; A61M 2205/18;
(Continued)

(56) References Cited

U.S. PATENT DOCUMENTS

| 5,808,181 A | 9/1998 | Wamsiedler et al. |
| 7,481,931 B2 | 1/2009 | Kiss et al. |

(Continued)

FOREIGN PATENT DOCUMENTS

| DE | 102013014751 | 3/2015 |
| DE | 102014014418 | 3/2016 |

(Continued)

OTHER PUBLICATIONS

International Search Report and Written Opinion in International Appln. No. PCT/EP2021/075284, mailed Dec. 21, 2021, 20 pages (with English translation).

*Primary Examiner* — Dirk R Bass
(74) *Attorney, Agent, or Firm* — Fish & Richardson P.C.

(57) ABSTRACT

The present disclosure relates to a method for identifying a type of filter, a class of filters, or a feature of a filter, wherein the filter includes a first filter compartment and a second filter compartment, which are separated by a filter medium. The method includes generating a pressure in a fluid on a first side of the filter medium via a first pressure source, measuring the pressure profile on the first side of the filter medium using a first pressure sensor as a first pressure profile and on the second side of the filter medium using a second pressure sensor as a second pressure profile, over time, evaluating both the first pressure profile and the second pressure profile to obtain an evaluation result, and assigning the filter to a type of filter, a class of filters, or identifying a feature of the filter.

25 Claims, 3 Drawing Sheets

(52) U.S. Cl.
CPC ............... *A61M 2205/3331* (2013.01); *A61M 2205/702* (2013.01)

(58) Field of Classification Search
CPC .. A61M 2205/3331; A61M 2205/6018; A61M 2205/702
See application file for complete search history.

(56) References Cited

U.S. PATENT DOCUMENTS

| | | |
|---|---|---|
| 8,298,427 B2 | 10/2012 | Ficheux et al. |
| 8,676,512 B2 | 3/2014 | Balschat et al. |
| 10,857,278 B2 | 12/2020 | Thys et al. |
| 2012/0298581 A1 | 11/2012 | Wehmeyer et al. |
| 2016/0051742 A1 | 2/2016 | Strohhofer et al. |
| 2016/0213829 A1 | 7/2016 | Klewinghaus |
| 2018/0228959 A1 | 8/2018 | Thys |
| 2022/0241475 A1 | 8/2022 | Frenzel |

FOREIGN PATENT DOCUMENTS

| | | |
|---|---|---|
| DE | 102019120171 | 1/2021 |
| EP | 0763367 | 3/1997 |
| EP | 1236479 | 5/2005 |
| EP | 1892000 | 2/2008 |
| EP | 1501568 | 7/2009 |
| EP | 2362790 | 5/2015 |
| EP | 2910261 | 11/2017 |
| WO | WO 2004/009157 | 1/2004 |
| WO | WO 2009/080258 | 7/2009 |
| WO | WO 2016/050339 | 4/2016 |

METHOD FOR IDENTIFYING THE TYPE OF A MEDICAL FILTER, AND APPARATUSES

CROSS-REFERENCE TO RELATED APPLICATIONS

The present application is the national stage entry of International Patent Application No. PCT/EP2021/075284, filed on Sep. 15, 2021, and claims priority to Application No. DE 102020124395.2, filed in the Federal Republic of Germany on Sep. 18, 2020, the disclosures of which are expressly incorporated herein in their entirety by reference thereto.

TECHNICAL FIELD

The present disclosure relates to a method as described herein, a control device as described herein, a medical apparatus as described herein, a digital storage medium as described herein, a computer program product as described herein, and a computer program as described herein.

BACKGROUND

In extracorporeal blood treatment, filters with semi-permeable membranes are used, for example in hemofiltration, hemodialysis, hemodiafiltration, plasmapheresis and other treatment options.

Different types of filters are often used for blood treatments with the same treatment options, even when the same blood treatment apparatus is always used. As the success of the treatment depends to a large extent on using a filter 30 of a suitable filter type for the treatment, it is essential to ensure that a filter of the correct filter type is used for the upcoming treatment before starting treatment. It is common for the operator of a treatment apparatus to equip it with a (mostly disposable) filter before the treatment session starts, which the operator supplies, e.g., taken from a supply or store. However, due to an error on the part of the operator, an incorrect or unsuitable filter may be inserted.

In the case of methods known from prior art, a mistake being made by the operator in their choice of filter is prevented in that the treatment apparatus, in which the filter is inserted or with which the filter is used, identifies the type of filter on the basis of external features of the filter, such as mechanical or optical features, and if the filter is not suitable for the upcoming treatment option, it takes measures (alarm, blocking of treatment options, etc.) thus preventing treatment with an unsuitable filter. The detection of these external features of a filter requires the use of at least one sensor or other component which is specifically designed for this filter type recognition.

In some aspects, the present disclosure proposes a further method for identifying the type of a medical filter, a class of filters, or a feature of a medical filter. Furthermore, suitable apparatuses should be specified.

SUMMARY

A method is disclosed herein for identifying a type of medical filter, a class of filters, or a feature of a medical filter. The medical filter(s) has/have at least a first filter compartment and a second filter compartment that are separated from each other by a filter medium.

The methods described herein can include generating or increasing a pressure in the fluid (fluid pressure), in particular a liquid, on a first side of the filter medium of a provided filter. This takes place using a first pressure source, for example a pump, whereby pressure is built up in the filter.

The methods can further include measuring the pressure profile over time both on a first side of the filter medium whereby a first pressure profile is obtained and also on a second side of the filter medium whereby a second pressure profile is obtained. The measuring occurs particularly during the pressure build-up or with built-up pressure. The measuring of the first pressure profile takes place using a first pressure sensor, which is arranged between the first pressure source and the filter. The measuring of the second pressure profile takes place using a second sensor.

The methods can further include an evaluation of both the first pressure profile and the second pressure profile. This evaluation results in obtaining at least one evaluation result.

The methods can further include assigning the medical filter which was exposed to the pressure as described above to a type of filter, a class of filters or, alternatively or additionally, the step of identifying a feature of the medical filter. The assigning takes place based on the at least one evaluation result.

For the purposes of assigning, the evaluation result can be compared with suitable reference values and/or measured against them.

Such reference values can be stored in a storage device suitable for this purpose, e.g., in a data memory, which in turn is part of a treatment apparatus. The storage device can be or include any of the embodiments of a storage device described herein.

Furthermore, the present disclosure relates to a control device configured, in interaction with a provided medical apparatus which includes a filter, a first pressure source, a first pressure sensor and a second pressure sensor—in particular as disclosed herein—in order to initiate or execute a method described herein.

An interaction may be or encompass an actuation, control or regulation. An interaction may be or require a signal connection.

The present disclosure further relates to a medical apparatus.

This apparatus can include a filter, a first pressure source, a first pressure sensor and a second pressure sensor. It can further include a control device as described herein. Alternatively, it is connected to the devices mentioned above.

A digital, particularly non-volatile storage medium, according to the present disclosure, particularly in the form of a machine readable carrier, particularly in the form of a diskette, memory card, CD, DVD, EPROM, FRAM (Ferroelectric RAM) or SSD (Solid-State-Drive), particularly with electronically or optically readable control signals, may be configured in order to configure a conventional control device into a control device as described herein, with which the method described herein may be initiated.

Thereby, all or part this method can be initiated.

A computer program product, according to the present disclosure, can include a volatile or transient program code or one stored on a machine readable carrier or a signal wave, via which a conventional control device may be configured into a control device according to the present disclosure with which the method according to the present disclosure may be initiated, when the computer program is running on a computer.

Thereby, all or part of this method can be initiated.

A computer program product, for example, can be understood according to the present disclosure as a computer program stored on a carrier, an embedded system being a comprehensive system with a computer program (e.g., electronic device with a computer program), a network of computer implemented computer programs (e.g., client/server-system, cloud computing system etc.), or a computer on which a computer program is loaded, runs, is stored, is executed or developed.

The term "machine readable carrier" as it is used herein, refers in certain embodiments to a carrier, which contains data or information interpretable by software and/or hardware. The carrier may be a data carrier, such as a diskette, a CD, DVD, a USB stick, a flashcard, an SD card or any other herein referred to storage medium.

A computer program, according to the present disclosure, can include a program code, via which a control device may be configured into a control device according to the present disclosure via which the method described herein may be initiated when the computer program runs on a computer.

Thereby, all or part of this method can be initiated.

According to the present disclosure, a computer program can be taken to mean a physical, for example, distributable software-product which includes a program.

In all of the statements made herein, the use of the expression "may be" or "may have" and so on, is to be understood synonymously with "preferably is" or "preferably has," and so on respectively, and is intended to illustrate an embodiment.

Whenever numerical words are mentioned herein, the person skilled in the art shall recognize or understand them as indications of a numerical lower limit. Unless it leads the person skilled in the art to an evident contradiction, the person skilled in the art shall comprehend the specification for example of "one" as encompassing "at least one". This understanding is also equally encompassed by the present disclosure as the interpretation that a numeric word, for example, "one" may alternatively mean "exactly one", wherever this is evidently technically possible for the person skilled in the art. Both understandings are encompassed by the present disclosure and apply herein to all used numerical words.

Whenever the term "programmed" or "configured" is mentioned herein, it is also disclosed that these terms are interchangeable with one another.

Whenever an embodiment is mentioned herein, it represents an exemplary embodiment according to the present disclosure.

When it is disclosed herein that the subject-matter according to the present disclosure includes one or several features in a certain embodiment, it is also respectively disclosed herein that the subject-matter according to the present disclosure explicitly does not include this or these features in other embodiments likewise according to the present disclosure, e.g., in the sense of a disclaimer. Therefore, for every embodiment mentioned herein it applies that the converse embodiment, e.g., formulated as negation, is also disclosed.

Embodiments according to the present disclosure may include one or more of the aforementioned and/or following features in any technically possible combination.

In several embodiments, a filter selected for use by the operator is assigned to a certain type or class of filter, and the so specified filter type to be used is compared with a general or factory filter type required or recommended for the specific medical apparatus or for the treatment option specifically planned with the apparatus. These embodiments may also provide that should the comparison reveal that the filter is not suitable for the preselected treatment option, it is an unauthorised filter type or similar, then the carrying out of the specifically planned treatment option preselected on the medical apparatus is automatically blocked by the medical apparatus, For example, if it is detected that a plasma filter was inadvertently connected instead of a dialyzer, a dialysis treatment can be blocked, or vice versa.

In some embodiments, the pressure profile is measured in a dialysis liquid or dialysate stream which flows through the filter or in a dialysis liquid or a dialysate with which the filter is in fluid connection.

In several embodiments, the method also includes outputting of an evaluation result, a consequence thereof or a corresponding signal based thereon. The output can be signal-bound, it can occur, for example, visually, audibly, etc.

In some embodiments of the method, the filter is a dialyzer or blood filter.

In several embodiments, the first pressure source is or includes a blood pump.

In some embodiments, the first filter compartment is a blood chamber and/or the second filter compartment is a dialysis liquid chamber.

In several embodiments, the filter medium is a semipermeable membrane or includes a multitude of such membranes.

In some embodiments, the second pressure sensor is located between a dialysis liquid pump and a dialysate pump of the medical apparatus. The dialysate pump can also be referred to as a filtrate pump or effluent pump.

In some embodiments, the pressure in the fluid is increased using the first pressure source until a predetermined pressure is reached. Thereby, upon reaching this pressure the first pressure source is preferably switched off or stops conveying, or the pressure is on some other way prevented from increasing (e.g., by closing a valve or by opening a bypass).

In several embodiments, the first pressure source conveys the fluid with a flow of at least 150 ml/min, preferably at least 180 ml/min, particularly preferably at least 200 ml/min, or is controlled accordingly.

In some embodiments, the first pressure source conveys the fluid for at least 5 seconds, preferably at least 8 seconds, more preferably at least 10 seconds, or is controlled accordingly.

In several embodiments, the pressure profile is measured using the first pressure sensor as well as the second pressure sensor, whilst the first pressure source conveys the fluid or is controlled accordingly.

In some embodiments, in order to achieve the evaluation result the evaluation encompasses or consists of smoothing, in particular via a median filter, the pressure profile measured using the first pressure sensor and/or the pressure profile measured using the second pressure sensor.

In several embodiments, in order to achieve the evaluation result the evaluation is or consists of forming a pressure difference profile between the pressure profile measured by the first pressure sensor and the pressure profile measured by the second pressure sensor.

In some embodiments, in order to achieve the evaluation result the evaluation encompasses the integration of the pressure difference profile over time or consists of it.

In several embodiments, the integration of the pressure difference profile is or consists of a numerical integration, preferably by applying the trapezoidal rule.

In some embodiments of the medical apparatus according to the present disclosure, the control device is further configured to output an alarm via an alarm device, which may be part of the medical apparatus, in order to prevent a treatment option via the medical apparatus, and/or to stop a pump of the medical apparatus, preferably a pump which conveys medical liquid, in particular dialysis liquid. According to the configuration, this occurs if the control device determines or establishes that the evaluation result and/or the result of the assigning does not meet a predetermined criterion.

In several embodiments, the criterion may take into account or be based on the treatment option set for the medical apparatus, or on the type of filter which is required for the treatment option.

In some embodiments of the medical apparatus according to the present disclosure, the control device is connected to an output device in signal connection for outputting an indication to the operator that the filter used is not of the required type, that treatment options are blocked, etc.

In some embodiments, the medical apparatus is designed as a blood treatment apparatus, blood purification apparatus or dialysis apparatus, as a filtration apparatus, a diafiltration apparatus or as a dialysis apparatus in any other configuration for blood purification which is known to the person skilled in the art such as hemodialysis, hemofiltration or hemodiafiltration. It may be a plasmapheresis apparatus.

In certain embodiments, the medical apparatus is configured for use for continuous venous hemodiafiltration (CVV-HDF) and/or for use in acute dialysis or as a critical care device.

In several embodiments, the method is performed and completed before a patient's treatment or examination by the medical apparatus is started. Preferably, it is performed and completed after the completion of filling or priming an extracorporeal blood circuit connected to the medical apparatus for an upcoming treatment or examination of the patient.

In some embodiments of the medical apparatus according to the present disclosure, the control device is configured to output an alarm via an alarm device, if the result of the evaluation result determines that the inserted filter is of a different type than intended or required.

Alternatively or additionally, the control device may be configured in such a case to prevent a treatment option via the medical apparatus and/or to stop a pump of the medical apparatus. Preferably this pump is a pump which conveys liquid, in particular dialysis liquid or blood through the filter.

In certain embodiments, the medical apparatus according to the present disclosure is connected to an extracorporeal blood circuit and/or a tubing system.

In some embodiments, a pressure profile is a sequence of at least 3, 5, 30, 50 or more measurements, or a sequence of measurements at 3, 5, 30, 50 or more time points. The time points can be within a maximum time period of 3, 5, 10, 15, 20 or more seconds.

In some embodiments, the method and in particular the evaluation do not encompass any determination and/or notification of an ultrafiltration constant.

In several embodiments, measuring the pressure profile on both the first side of the filter medium and the second side of the filter medium does not represent the measurement of a transmembrane pressure.

In several embodiments, evaluating both the first pressure profile and the second pressure profile in order to obtain at least one evaluation result does not lead to the output or communication of the level of the transmembrane pressure.

In several embodiments, the method does not encompass measuring and/or a communicating the transmembrane pressure 30 and/or a flow resistance of the filter.

In some embodiments, only the measurement of the second pressure profile takes place on the hydraulic side of the medical apparatus. The first pressure profile is measured on the blood side or the side of the blood tubing set.

In several embodiments, for the evaluation the pressure of the first pressure profile and/or of the second pressure profile is used during an increase in the respective pressure (possibly after smoothing), not during a decrease (possibly after smoothing) of the pressure or pressure profile. If, for example, the pressure curve initially rises over time (increase in pressure along a ascending section of the curve) and then falls again after a maximum pressure has been reached (drop in pressure along a descending section of the curve), so the pressure is observed in the ascending section, not in the descending section.

Several or all of the embodiments according to the present disclosure may have one, several or all of the advantages mentioned above and/or below.

The present methods, devices, and systems are easily implemented in existing systems because filling and rinsing is carried out as standard prior to a treatment session and thus, according to the present disclosure, use can be made of equipment already present on a treatment device, such as a blood pump, dialysate pump, pressure sensors, tubing clamps, etc.

Using the method described herein, an automatic check of the filter type can be carried out before the start of the treatment which as a result can output a statement as to whether or not the connected filter is suitable for the upcoming treatment. Patient safety can be significantly increased in that in the case of unsuitability, it may be provided for that the preselected treatment option is automatically blocked.

Using the present methods, devices, and systems, it may be possible to distinguish very reliably between filters/dialyzers, even between filters or dialyzers whose distinguishable characteristics are very alike or very similar to each other. This advantageously contributes to increasing patient safety.

The implementation of the teaching according to the present disclosure does not require a mechanical solution in the sense of moving parts which can make it robust, simple to design and requires minimal maintenance. A considerable advantage of the present methods, devices, and systems is that the patient is protected even before the medical apparatus is used for treatment or examination.

BRIEF DESCRIPTION OF THE DRAWINGS

In the following, the present invention is exemplarily explained with regard to the accompanying drawing in which same reference numerals refer to the same or similar components. In the figures of the drawing the following applies.

DETAILED DESCRIPTION

Figure 1:
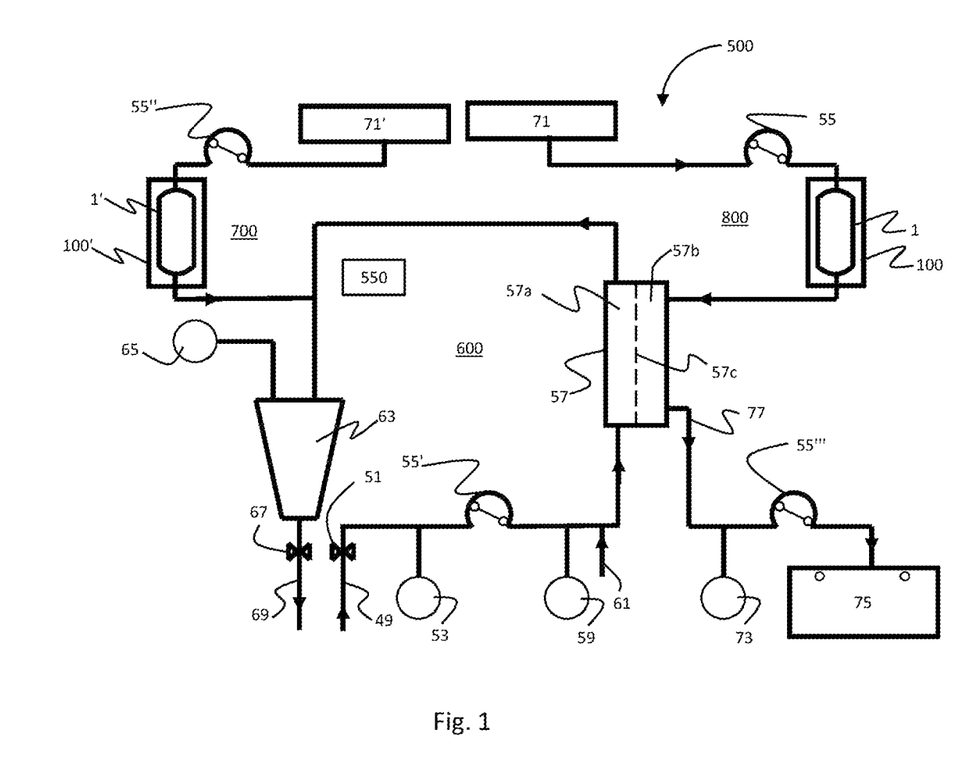
FIG. 1 shows in highly simplified representation, a procedure flow chart of a medical apparatus, here a blood treatment apparatus.

FIG. 1 shows in a highly simplified representation, a procedure flow chart of an exemplary medical apparatus 500, here a blood treatment apparatus.

The medical apparatus 500 is optionally connected to an extracorporeal blood circuit 600 and further optionally connected to an effluent bag 75.

The extracorporeal blood circuit 600 includes a first line 49, here in the form of an arterial line section.

The first line 49 is optionally in fluid communication with a blood treatment apparatus, here for example a blood filter or a dialyzer 57. The blood filter 57 includes a dialysis liquid chamber 57b and a blood chamber 57a, which are separated from each other by a mostly semi-permeable membrane 57c.

The extracorporeal blood circuit 600 further includes at least one second line 69, here in the form of a venous line section. Both the first line 49 and the second line 69 may be used to connect them to the vascular system of the patient, not shown.

The first line 49 is optionally connected to a (first) tubing clamp 51 for blocking or closing the line 49. The second line 69 is optionally connected to a (second) tubing clamp 67 for blocking or closing the line 69.

The blood treatment apparatus 500 represented in FIG. 1 only schematically and only by some of its devices includes a blood pump 55'. During the patient's treatment, the blood pump 55' conveys blood through sections of the extracorporeal blood circuit 600 and towards the blood filter or dialyzer 57, as indicated by the small arrows. Prior to a treatment session, the blood pump 55' is used to fill and rinse parts of the medical device 500 and sections of the extracorporeal blood circuit 600 with liquid.

Fresh dialysis liquid is pumped, e.g., from a source 71 along the dialysis liquid inlet line into the dialysis liquid chamber of the blood filter 57, by a pump 55 for dialysis liquid, which may be designed as a roller pump, as an otherwise occluding pump or as a membrane pump or an impeller pump. The dialysis liquid tubing set has the reference numeral 800. The dialysis liquid leaves the dialysis liquid chamber as dialysate, possibly enriched by filtrate, through the dialysate outlet line towards the optional effluent bag 75 or to a drain and is herein referred to as effluent.

The effluent may be discarded from the optional effluent bag 75 via an effluent outlet line into a drain. In several embodiments the effluent is directly discarded via a dialysate outlet line into a drain (not shown here).

The source 71 may be, for example a bag or a container. The source 71 may further be a fluid line out of which online and/or continuously generated or mixed liquid is provided, for example a hydraulic outlet or hydraulic port of the medical apparatus 500.

The dialysis liquid inlet line of FIG. 1 optionally includes or is connected to a heater bag 1. The heater bag 1 is placed in a first heating device 100 to supply heated dialysis fluid to the blood filter 57. This serves to counteract a cooling down of the patient being treated.

A further source 71 with substitute may be optionally provided. It may correspond to the source 71 or be a separate source.

Also a substitute line leading from the source 71' to the extracorporeal blood circuit 600 may include or be connected to a heater bag 1. The substitute tubing set has the reference numeral 700. The second heater bag 1' may be inserted in a second heating device 100 in order to supply heated substitute to the extracorporeal blood circuit 600. This likewise serves to counteract a cooling down of the patient being treated.

In addition to the aforementioned blood pump 55' and the pump 55 for dialysis liquid, the arrangement shown in FIG. 1 further includes purely optionally a series of other pumps, in each case optional, namely the pump 55" for substituate, and the pump 55'" for the effluent (also referred to as filtrate pump or dialysate pump).

Upstream of blood pump 55' an optional arterial sensor 53 is provided. It measures the pressure in the arterial line, during the patient's treatment.

Downstream of the blood pump 55', but upstream of the blood filter 57 and, if provided, preferably upstream of an addition point 61 for anticoagulant, for example heparin, a further optional pressure sensor 59 is provided. It measures the pressure upstream of the blood filter 57 ("pre-hemofilter").

Again, a further pressure sensor 73 may be provided downstream of the blood filter 57, however preferably upstream of the pump 55'", in the dialysate outlet line in order to measure the filtrate pressure of the blood filter 57.

An only roughly indicated control device or closed-loop control device 550 is configured to execute or initiate a method as described herein. It can optionally be further configured to control or regulate the medical apparatus 500, for example for the treatment of the patient. It can be in cable or wireless signal communication with any of the components referred to herein—especially or in particular the blood pump 55' and the pressure sensor 59 and 73—in order to control or regulate the blood treatment apparatus 100 and in particular the pressure in the arterial line 49 and in the blood filter 57.

Blood, which leaves the blood pump 57, passes through an optional venous blood chamber 63, which can include a de-aeration device and may be in fluid communication with a further pressure sensor 65 in order to measure the venous pressure.

Figure 2:
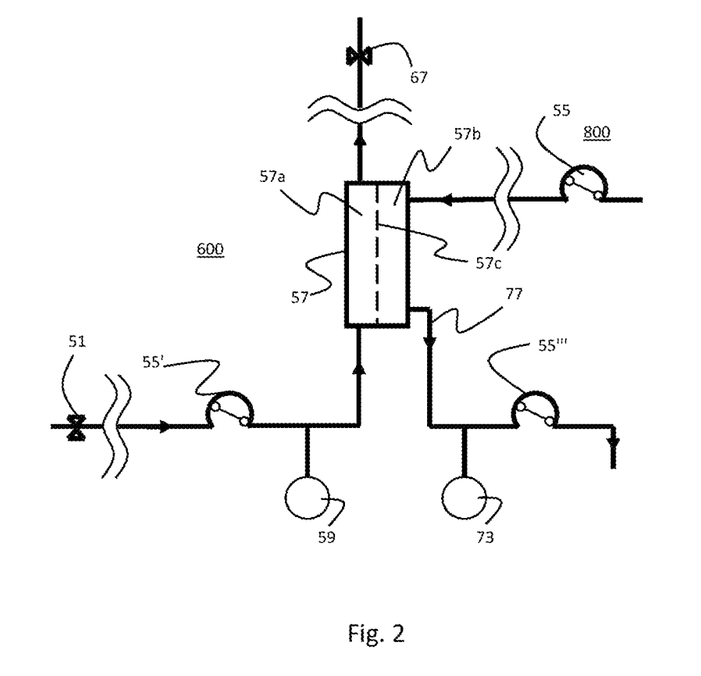
FIG. 2 shows a section of the medical apparatus of FIG. 1, having the apparatuses necessary for carrying out a method according to the present disclosure.

FIG. 2 shows a section of the medical apparatus 500 of FIG. 1, having the apparatuses necessary for carrying out a method described herein.

A prerequisite for carrying out a method according to the present disclosure is filling the tubing set 600, 800 as well as the dialysate outlet line 77, which is not part of the method described herein.

The following is an example of the generation of a pressure profiles while simultaneously measuring the pressures or pressure profile within the scope of the method described herein.

For this purpose, firstly some or all of the aforementioned pumps in the aforementioned tubing sections, in particular the blood pump 55', the dialysis liquid pump 55 and the dialysate pump 55'", are preferably halted. In most embodiments, the halted or non-delivering pumps sufficiently close the corresponding tubing lines, since they are regularly designed as occluding pumps.

The venous tubing clamp 67 is preferably closed and the arterial tubing clamp 51 is opened. After a short waiting period, of for example a second, the blood pump 55", initiated via the control device 550, starts to operate with a predetermined flow rate of preferably approx. 200 ml/min and operates for a predetermined time period, e.g., ten seconds. This comparatively high flow through the blood pump 55' is used to generate a clearly measurable pressure profile 1000 or 2000 (see FIG. 3a and FIG. 3b). The blood pump 55' is then halted.

During the pumping process the pressure values from both pressure sensors 59 (pre-filter) and 73 (filtrate) and thereby on each side of the filter medium, here a semi-permeable membrane 57c, are recorded and preferably stored on a storage device (not shown in FIG. 2). The pressure values determined serve as raw data for the evaluation which is described in more detail in connection with FIGS. 3a and 3b. They are preferably recorded using the unit [mmHg].

It can also be ensured that after measuring the pressures as described herein the tubing system of the medical treatment apparatus 500 is largely relieved of pressure.

For this purpose, after a further short waiting period of for example 5 seconds or more, the venous tubing the venous tubing clamp 67 can be opened and the dialysate pump 55''' can begin to operate with a predetermined flow rate for example of approx. 200 ml/min, for a predetermined time period, e.g., ten seconds.

After a further waiting period of preferably ten seconds, both tubing clamps 51 and 67 may be finally closed again.

Figure 3A:
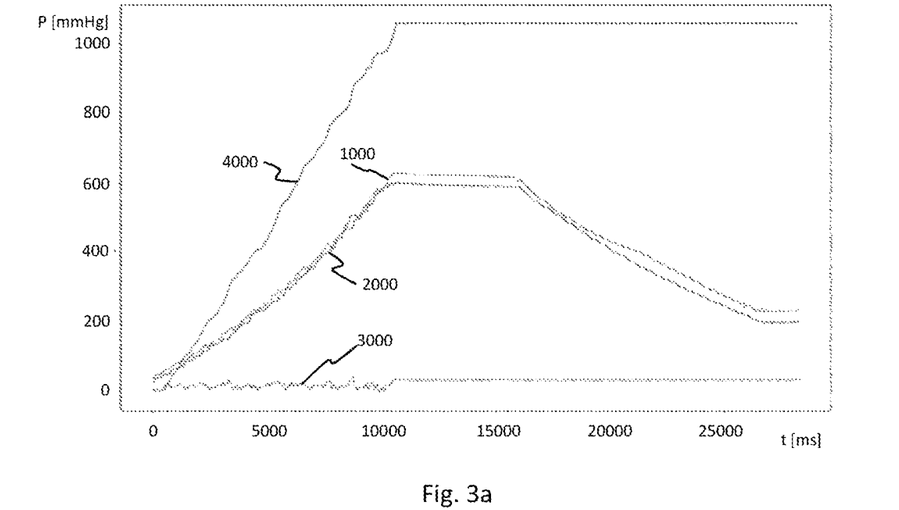
FIG. 3a shows a first example for the recording of pressure profiles and their evaluation.

FIG. 3a shows a first example for measuring a first and a second pressure profile on a filter of a first type, here a plasma filter as an example. The two pressure profiles are shown in the diagram as possibly pre-set pressure profile curves 1000 or 2000 over time t (in the unit [ms]), their evaluations as curves 3000 or 4000 respectively.

The evaluation takes place after measuring the pressures, e.g., using the components shown in FIG. 2 in the context of the method as described above. In FIG. 3a the measured pressures are shown as pressure profile curves 1000, 2000 over time.

In this example, the determined pressure profiles were advantageously smoothed out using a mathematical filter, here for example using a median filter, preferably of the order 11. This for example may then serve, to eliminate the deviations in the determined values which were generated by the blood pump. The previously referred to smoothing procedure is purely exemplary and is not limited to a median filter of the order 11.

An absolute maximum, as well as its position or time of occurrence within the pressure measurement values can optionally be determined from the smoothed values or in some other way. The maximum defines the end of the pressure increase and with it the time at which the blood pump 55' is switched off or the time at which for other reasons the pressure was not further increased. Preferably the pressure profiles up to this maximum, i.e., the pressure increase, are relevant for the evaluation. It would be best not to integrate the pressure values or their differences formed after this maximum.

A difference curve 3000 can be calculated from the pressure profile 1000 (pre-filter) and the pressure profile 2000 (filtrate), in particular up until the time point of the maximum, in that for each common measurement point in time the difference is determined between the two corresponding pressure measurement values, which were measured by the pressure sensors 59 or 73. If this difference 3000 is integrated numerically, for example using the trapezoidal method, it results in an integration curve 4000.

In the example shown, this integration curve 4000 shows a positive gradient.

The profile of the integration curve 4000 can serve to be used to assign the filter under consideration to a filter class or a filter type, since, according to the inventor's knowledge, the procedure of the pressure evaluation described here for different filter classes leads to different integration curves.

Figure 3B:
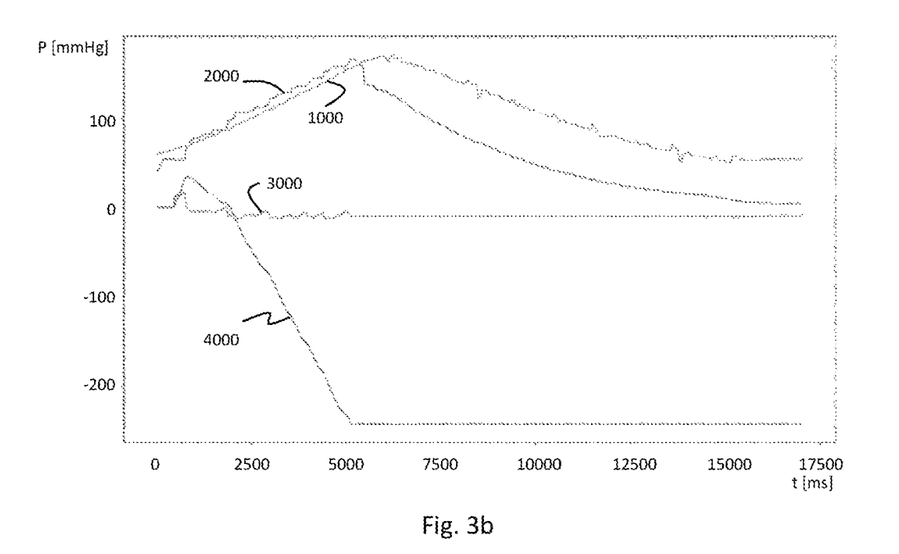
FIG. 3b shows a second example for the recording of pressure profiles and their evaluation.

FIG. 3b shows a second example for the recording of pressure profiles based on a second filter type, here exemplarily a blood filter or dialyzer for continuous renal replacement therapy (CRRT).

All of the above in FIG. 3a equally applies to FIG. 3b. However, in this example the integration curve 4000 shows a negative gradient.

The result of the integration can therefore be used to make a statement about the filter or filter type inserted by comparing the result of the integration with reference integration results of known filter types. In general, a distinction between plasma and CRRT filters is already possible by the algebraic sign of the result. A positive sign indicates a plasma filter, otherwise a CRRT filter is indicated. In several embodiments, the absolute value of the result can also be used to make a more detailed statement about the filter, for example the specific filter model can be named.

LIST OF REFERENCE NUMERALS

1, 1' heater bag
49 first line; arterial line section
51 tubing clamp, arterial
53 pressure sensor for arterial pressure
55 dialysis liquid pump
55' blood pump
55" substituate pump
55''' dialysate pump; filtrate pump; effluent pump
57 blood filter; dialyzer
57a blood chamber
57b dialysis liquid chamber
57c semi-permeable membrane
59 pressure sensor for hemofiltration pressure
61 addition point for anticoagulant
63 venous drip chamber
65 pressure sensor for venous pressure
67 tubing clamp, venous
69 second line; venous line section
71 liquid source (dialysis liquid)
71' liquid source (substituate)
73 pressure sensor for filtrate pressure
75 effluent bag
77 dialysate outlet line
100 first heating device
100' second heating device
500 medical apparatus
550 control device or closed-loop control device
600 extracorporeal blood circuit
700 substituate tubing set
800 dialysis liquid tubing set
1000 first pressure profile (pre-filter)
2000 second pressure profile (filtrate)
3000 difference between the first and second pressure profile; difference curve
4000 numerical integration of the difference between first and second pressure profile; integration curve

The invention claimed is:

1. A method for identifying a type of a medical filter or a class of filters, wherein the medical filter comprises a first filter compartment and a second filter compartment that are separated from each other by a filter medium, the method comprising:
  generating a pressure in a fluid at a first side of the filter medium via a first pressure source so that the medical filter is exposed to the pressure;
  measuring, over time, a first pressure profile at the first side of the filter medium using a first pressure sensor arranged between the first pressure source and the medical filter;
  measuring, over time, a second pressure profile at a second side of the filter medium using a second pressure sensor;
  evaluating both the first pressure profile and the second pressure profile to obtain at least one evaluation result, wherein evaluating both the first pressure profile and the second pressure profile comprises forming a pressure difference profile between the first pressure profile measured by the first pressure sensor and the second pressure profile measured by the second pressure sensor, and wherein evaluating both the first pressure profile and the second pressure profile comprises integrating of the pressure difference profile over time; and assigning, to the medical filter, the type of filter or the class of filters based on the at least one evaluation result.

2. The method according to claim 1, wherein the fluid is a liquid.

3. The method according to claim 1, wherein the filter comprises a dialyzer or a blood filter; and/or wherein the first pressure source comprises a blood pump; and/or wherein the first filter compartment comprises a blood chamber and the second filter compartment comprises a dialysis liquid chamber; and/or wherein the filter medium comprises a semipermeable membrane.

4. The method according to claim 1, wherein the second pressure sensor is arranged between a dialysis liquid pump and a dialysate pump of a medical apparatus.

5. The method according to claim 1, wherein the first pressure source increases the pressure in the fluid until a predetermined pressure is reached.

6. The method according to claim 5, wherein upon the predetermined pressure being reached the first pressure source is switched off or stops conveying.

7. The method according to claim 1, wherein the first pressure source conveys the fluid with a flow of at least 150 ml/min.

8. The method according to claim 1, wherein the first pressure source conveys the fluid with a flow of at least 180 ml/min.

9. The method according to claim 1, wherein the first pressure source conveys the fluid with a flow of at least 200 ml/min.

10. The method according to claim 1, wherein the first pressure source conveys the fluid for at least 5 seconds.

11. The method according to claim 1, wherein the first pressure source conveys the fluid for at least 8 seconds.

12. The method according to claim 1, wherein the first pressure source conveys the fluid for at least 10 seconds.

13. The method according to claim 1, wherein the pressure profile is measured using the first pressure sensor as well as the second pressure sensor whilst the first pressure source conveys the fluid.

14. The method according to claim 1, wherein evaluating the first pressure profile comprises smoothing the pressure profile measured using the first pressure sensor and/or evaluating the second pressure profile comprises smoothing the pressure profile measured using the second pressure sensor.

15. The method according to claim 14, wherein smoothing the pressure profile comprises smoothing the pressure profile via a median filter.

16. A control device configured, in interaction with a provided medical apparatus, which comprises a filter, a first pressure source, a first pressure sensor and a second pressure sensor, to initiate or implement a method comprising:

generating a pressure in a fluid at a first side of a filter medium of the filter via the first pressure source, so that the filter is exposed to pressure;

measuring, over time, a first pressure profile at the first side of the filter medium using the first pressure sensor, wherein the first pressure sensor is arranged between the first pressure source and the filter;

measuring, over time, a second pressure profile at a second side of the filter medium using the second pressure sensor;

evaluating both the first pressure profile and the second pressure profile in order to obtain at least one evaluation result, wherein evaluating both the first pressure profile and the second pressure profile comprises forming a pressure difference profile between the first pressure profile measured by the first pressure sensor and the second pressure profile measured by the second pressure sensor, and wherein evaluating both the first pressure profile and the second pressure profile comprises integrating of the pressure difference profile over time; and assigning, to the medical filter, a type of filter or a class of filters based on the evaluation result.

17. A medical apparatus comprising a filter, a first pressure source, a first pressure sensor and a second pressure sensor, and wherein the medical apparatus further comprises a control device according to claim 16 or is connected respectively thereto.

18. The medical apparatus according to claim 17, wherein the control device is further configured to output an alarm via an alarm device to prevent a treatment via the medical apparatus, and/or to stop a pump of the medical apparatus if the control device determines that the evaluation result and/or the result of the assigning does not meet a predetermined criterion.

19. The medical apparatus according to claim 18, wherein the pump of the medical apparatus conveys medical liquid.

20. The medical apparatus according to claim 19, wherein the medical liquid is dialysis liquid.

21. The medical apparatus according to claim 17, wherein the medical apparatus comprises a blood treatment apparatus, blood purification apparatus, plasmapheresis device, or dialysis apparatus, for hemodialysis, hemofiltration or hemodiafiltration.

22. A digital storage medium with electronically readable control signals, configured in order to configure a control device into the control device according to claim 16.

23. The digital storage medium of claim 22, wherein the digital storage medium comprises a diskette, CD or DVD or EPROM.

24. A computer program-product having a program code stored on a machine readable carrier in order to configure a control device into the control device according to claim 16.

25. A computer program with a program code in order to configure a control device into the control device according to claim 16.

* * * * *